United States Patent [19]

Havera et al.

[11] 4,061,760
[45] Dec. 6, 1977

[54] METHOD FOR USING 3-SUBSTITUTED-5-PHENYL-5-PYRIDYL HYDANTOINS AS ANTIARRHYTHMIC AGENTS

[75] Inventors: Herbert John Havera, Edwardsburg, Mich.; Wallace Glenn Strycker, Goshen, Ind.

[73] Assignee: Miles Laboratories, Inc., Elkhart, Ind.

[21] Appl. No.: 729,164

[22] Filed: Oct. 4, 1976

Related U.S. Application Data

[62] Division of Ser. No. 664,920, March 8, 1976, Pat. No. 3,994,904.

[51] Int. Cl.$^2$ .......................................... A61K 31/445
[52] U.S. Cl. ................................... 424/267; 260/293.7
[58] Field of Search ........................................... 424/267

[56] References Cited

U.S. PATENT DOCUMENTS

| | | | |
|---|---|---|---|
| 2,526,231 | 10/1950 | Henze | 260/295 |
| 3,892,748 | 7/1975 | Hayao et al. | 260/293.7 |

OTHER PUBLICATIONS

Casagrande "Il Farmaco Ed. Sci." vol. 29, pp. 757-785 (1974).

*Primary Examiner*—Natalie Trousof
*Assistant Examiner*—Robert T. Bond
*Attorney, Agent, or Firm*—Joseph C. Schwalbach; Richard W. Winchell

[57] ABSTRACT

Compounds having the generic structure,

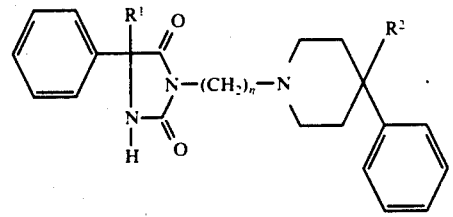

and their nontoxic, pharmacologically acceptable salts are useful in the chemotherapy of arrhythmias in individuals for whom such therapy is indicated. In the preceding structural formula: $R^1$ is a 2-pyridyl, 3-pyridyl, or 4-pyridyl radical; $n$ is an integer of the set 1–3; and $R^2$ is a hydrogen atom, a hydroxyl, or an equivalent alkoxyl group having from 1 to 3 carbon atoms.

10 Claims, No Drawings

METHOD FOR USING 3-SUBSTITUTED-5-PHENYL-5-PYRIDYL HYDANTOINS AS ANTIARRHYTHMIC AGENTS

This is a division of application Ser. No. 664,920, filed Mar. 8, 1976, now U.S. Pat. No. 3,994,904.

BACKGROUND OF THE INVENTION

1. Field of the Invention

Cardiac arrhythmias are disorders of impulse generation that result fro disruptions of normal cardiac pacemaker activity, from disturbances in cardiac conductive fibers, or from a combination of both preceding factors. Cardiac arrhythmias of clinical significance in man include: premature contractions (extrasystoles) originating in atrial or ventricular foci; paroxysmal supraventricular tachycardia; atrial flutter; atrial fibrillation; ventricular tachycardia; and ventricular fibrillation. Arrhythmias can be induced in laboratory animals that are suitable experimental models of man to study physiological mechanisms of the disorder or to screen new antiarrhythmic agents.

Clinical treatment of arrhythmias includes administration of a variety of drugs, although quinidine, procainamide, and diphenylhydantoin are current mainstays.

Quinidine is the d-isomer of quinine:

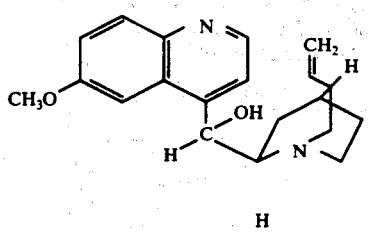

while procainamide is p-amino-N-(2-diethylaminoethyl)benzamide:

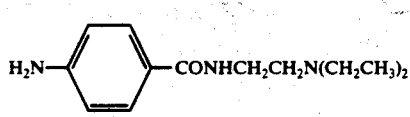

I and II require extreme care in administration because they are relatively toxic. In weighing their efficacy over their toxicity, however, the former is countervailing. Because of limitations in those antiarrhythmic drugs, there have been efforts to discover safer substitutes. The discovery of the antiarrhythmic activity of diphenylhydantoin opened new approaches in the design of new compounds exhibiting such activity.

Diphenylhydantoin (5,5-diphenyl-2,4-imidazolidinedione; "DPH"),

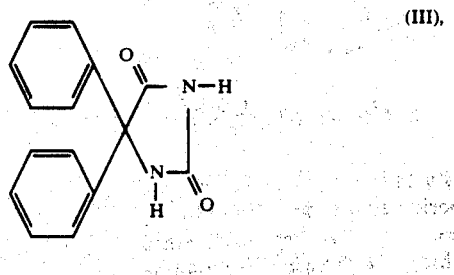

initially was utilized in the treatment of epilepsy but later was discovered to have important antiarrhythmic applications. The pharmacodynamics of DPH differ from those of quinidine and of procainamide, and DPH does not exhibit the toxic properties of either drug. DPH specifically antagonizes ventricular arrhythmias induced by digitalis, depresses ventricular automaticity, enhances atrio-ventricular modal conduction, and reduces the effective refractory period. DPH, however, is not without untoward side effects: dizziness, nausea, emesis, nystimus, and ataxia. Large doses of DPH may produce atrio-ventricular blockage, bradycardia, or even cardiac arrest. For a review of the current status of the field and of DPH as an antiarrhythmic agent, see: G. K. Moe and J. A. Albildskow, "Antiarrhytmic Drugs", in: *The Pharmacological Basis of Therpeutics*, 4th Edition, L. S. Goodman and A. Gilman, Editors, MacMillan Company, New York, Chapter 32 (1970); and L. S. Dreifus and Y. Watanabe, Amer. Heart J., 80: 709-713 (1970).

DESCRIPTION OF THE PRIOR ART

Relevant to the present are the following references: H. Henze, U.S. Pat. No. 2,526,231 (Oct. 17, 1950; "Henze"); and C. Casagrande et al., II. Farmaco Ed. Sc., 29: 757 (1974; "Casagrande").

Henze discloses synthesis of 5-phenyl-5-pyridyl hydantoins having the common structure,

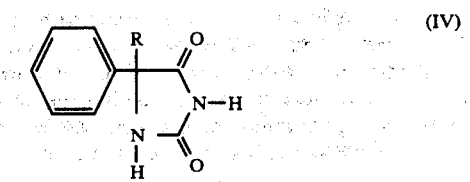

in which R is a 2-pyridyl, 3-pyridyl, or 4-pyridyl group, by reaction of an appropriate arylpyridylketone with a system comprising an alkali-metal cyanide, ammonia, carbon dioxide, and water in an inert organic solvent at temperatures of 100° to 150° C in a reaction bomb. The Henze patent contains three specific examples of IV that are used as starting materials for the compounds of the present invention and as reference compounds for comparative pharmacological tests: 5-phenyl-5-(2-pyridyl)-hydantoin (V); 5-phenyl-5-(3-pyridyl)-hydantoin (VI); and 5-phenyl-5-(4-pyridyl)-hydantoin (VIII). While Henze teaches that compounds IV-VII exhibit anti-convulsant activity and are useful in the treatment of epilepsy, it contains no express or implied disclosure relating to use of compounds IV-VII as antiarrythmic agents.

Casagrande describes certain 3-substituted-5-phenyl-5-pyridyl-hydantoin derivatives of the structural formula,

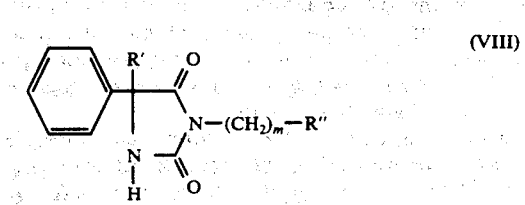

in which: R' is a 2-pyridyl, 3-pyridyl, or 4-pyridyl moiety; m is an integer having a value of 1 or 2; and R" is a dimethylamino, diethylamino, or piperidino group.

The reference, however, discloses no compounds in which R" is a 4-phenyl-piperidino, 4-phenyl-4-hydroxy-piperidino, or 4-phenyl-4-alkoxy-piperidino substituent. Although Casagrande teaches that compounds VII exhibit antiarrhythmic activity, it discourages further investigation in 3-substituted-5-phenyl-5-pyridyl-hydantoin analogues. Casagrande reports that when substituent R" of VIII is piperidino, antiarrhythmic activity is diminished: "Other modification, which resulted in lower activity, were as follows: . . . (b) substituting the piperidino for the demethylamino group . . . ." (II Farmaco, Ed. Sc., 29: 757 at 775 [1960]; emphasis added). Casagrande also indicates that none of compounds VII have a therapeutic index greater than that of quinidine: "Among the compounds examined, the β-pyridyl derivatives [3-(2-dimethylamino-ethyl)-5-phenyl-5β-pyridyl-hydantoin; compound XXV in Casagrande] and [3-(2-methyl-3-dimethylamino-propyl)-5-phenyl-5β-pyridyl-hydantoin; compound XXX in Casagrande] appeared to deserve further investigation . . . . However, on the basis of an overall appraisal of the pharmacological results, it was concluded that what we estimate to be the most important prerequisite of any improved antiarrhythmic agents [sic], i.e., a therapeutic index clearly superior to that of quinidine, had not been fulfilled either by compound XXV or XXX . . . (ibid. emphasis added)".

The compounds of the present invention are novel over the Henze and Casagrande references. Furthermore, Example 6 of this specification demonstrates that the claimed compounds are nonobvious in view of those references and provide technical advance in the field: they are very active notwithstanding the presence of a substituted piperidino moiety and exhibit therapeutic indices significantly superior to quinidine.

SUMMARY OF THE INVENTION

The subject matter of this invention is:
1. compounds and their nontoxic, pharmacologically acceptable salts having the generic formula,

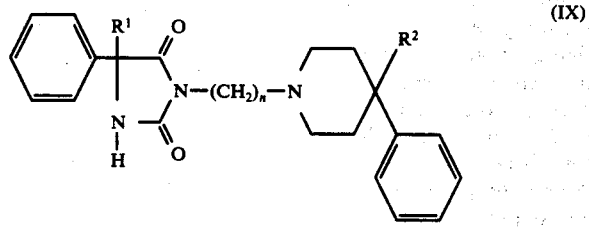

in which: $R^1$ is a 2-pyridyl, 3-pyridyl, or 4-pyridyl radical; n is an integer of the set 1-3; and $R^2$ is a hydrogen atom, a hydroxyl or an equivalent alkoxy group of 1 to 3 carbon atoms; and 2. an improved chemo-therapeutic method of treating an arrhythmia in an individual, the improvement comprising administering by conventional means to the individual an effective antiarrhythmic amount of a compound having structure IX, or a nontoxic pharmalogically acceptable salt thereof.

Compounds IX are antiarrhythmic agents that demonstrate superior therapeutic indices to that of quinidine and to the prior art compounds described in Henze and Casagrande; supporting data are found in Example 6, below.

A preferred subgenus of IX are compounds having the structure,

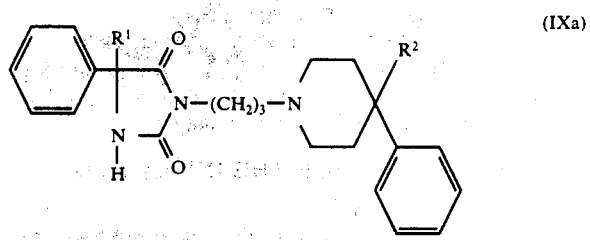

in which $R^1$ is 2-pyridyl, 3-pyridyl, or a 4-pyridyl radical and $R^2$ is a hydrogen atom or a hydroxyl group.

Synthesis of compounds IX is straight-forward as reference to Table A indicates. Reaction of an appropriate 5-phenyl-5-pyridyl hydantoin, X, with an 1-(ω-chloroalkyl) derivative of a 4-phenyl-piperidine, 4-hydroxy-4-phenyl-piperidine or 4-alkoxy-4-phenyl-piperidine, XI, in the presence of sodium ethoxide, sodium hydride, or sodium amide in an inert organic solvent at reflux temperatures for 2-18 hours yields a corresponding 3-substituted-5-phenyl-5-pyridyl hydantoin, IX. A variety of inert organic solvents are used in the synthesis including but not limited to ethanol, dimethylformamide, benzene, toluene, or xylene. Reflux temperatures depend upon the solvent utilized.

Starting materials X are 5-phenyl-5-(2-pyridyl)-hydantoin, 5-phenyl-5-(3-pyridyl)-hydantoin, and 5-phenyl-5-(4-pyridyl)-hydantoin. Henze (U.S. Pat. No. 2,526,277) describes the synthesis of starting materials X from appropriate phenyl-pyridylketones.

TABLE A

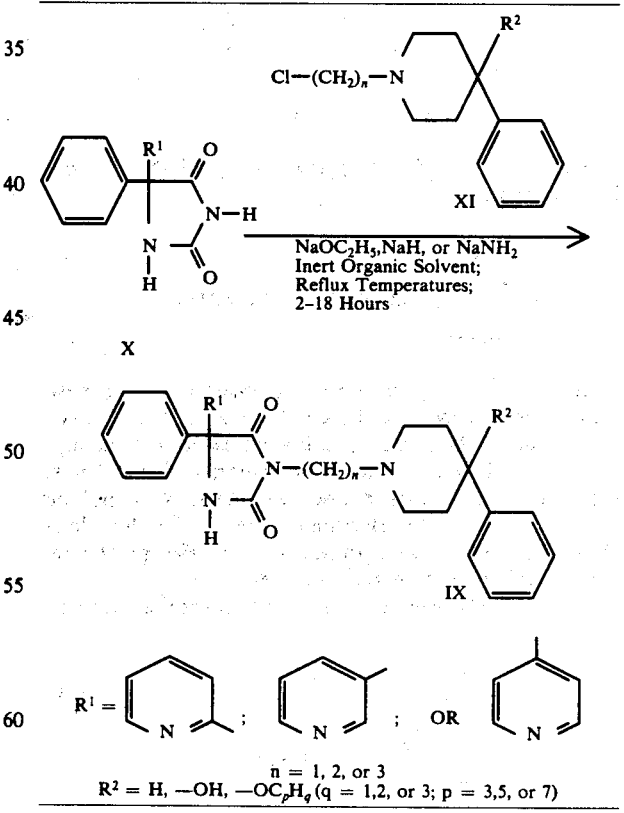

Starting materials XI are: 1-chloromethyl-4-phenyl-piperidine, 1-chloromethyl-4-hydroxy-4-phenyl-piperidine, 1-chloromethyl-4-methoxy-4-phenyl-piperidine, 1-chloromethyl-4-propoxy-4-phenyl-piperidine, 1-(2- chloroethyl)-4-phenyl-piperidine, 1-(2-chloroethyl)-4-hydroxy-4-phenyl-piperidine, 1-(2-chloroethyl)-4-methoxy-4-phenyl-piperidine, 1-(2-chloroethyl)-4-propoxy-4-phenyl-piperidine, 1-(3-chloropropyl)-4-phenyl-piperidine, 1-(3-chloropropyl)-4-hydroxy-4-phenyl-piperidine, 1-(3-chloropropyl)-4-methoxy-4-phenyl-piperidine, 1-(3-chloropropyl)-4-propoxy-4-phenyl-piperidine.

Materials XI, in turn, are prepared by reacting an appropriate 1-bromo-ω-chloro-alkane, XII, with a 4-substituted-piperidine, XIII:

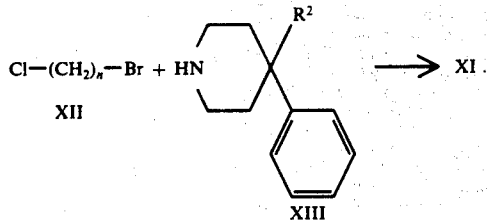

In the preceding synthetic pathway symbols n and $R^2$ have the same definition as established above. Compounds XII clearly are bromochloromethane, 1-bromo-2-chloro-ethane, and 3-bromo-1-chloro-propane. Materials XIII are 4-phenyl-piperidine, 4-hydroxy-4-phenyl-piperidine, 4-methoxy-4-phenyl-piperidine, and 4-propoxy-4-phenyl-piperidine. Compounds XII and XIII are commercially available.

Table B presents an alternate method of preparing compounds IX adapted from that disclosed in Casagrande: reaction of a 3-(ω-chloroalkyl)-5-phenyl-5-pyridyl-hydantoin, XIV, with an appropriate 4-substituted-piperidine, XIII (see preceding paragraph), in an inert organic solvent at reflux temperatures for 2-18 hours yields the desired compounds IX. Compounds XIV are prepared by well known N-3 alkylation reactions of materials X and XII, identified above.

TABLE B

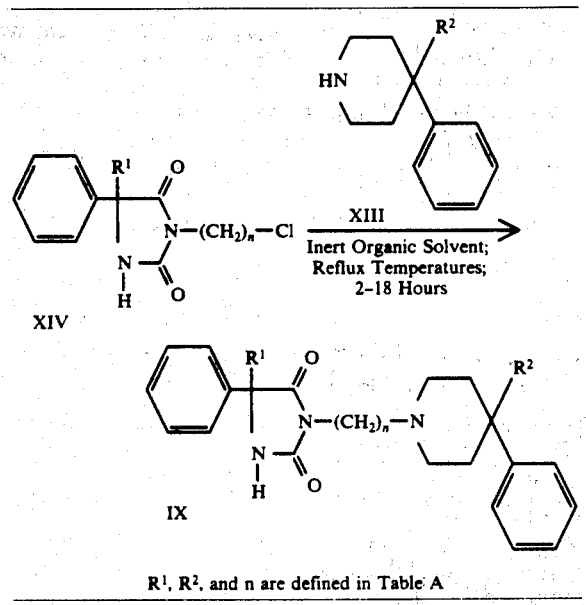

$R^1$, $R^2$, and n are defined in Table A

Nontoxic, pharmacologically acceptable salts forms of IX are prepared by conventional means from maleic, hydrochloric, succinic, lactic, citric and other acids as well as from methyl iodide.

The second subject matter of this invention is an improved method of chemotherapy (i.e., by use of DPH or its derivatives) of arrhythmias in individuals in whom that therapy is indicated. That improvement comprises administering to the individual a therapeutically effective amount of a compound having structure IX or a pharmacologically acceptable, nontoxic salt thereof. In the preceding sentence as elsewhere hereafter: "Individual" means a human being or a laboratory animal that is a suitable model for a human being; and "therapeutically effective amount" means a dose or series of doses that correct the arrhythmia to normal or near normal cardiac rhythm. The therapeutically effective amount will vary from individual to individual and will depend upon the nature of the arrhythmia, but it is easily determined by one skilled in the art without undue experimentation. Usually that amount may range from 5 to 500 mg/day.

Forms of IX suitable for administration are prepared by usual methods employed in the pharmaceutical arts for conventionally recognized modes of administration. Those modes of administration are oral, buccal, sublingual, rectal, parenteral, or intramuscular.

DESCRIPTION OF THE PREFERRED EMBODIMENTS

In the following examples: "DMF" is dimethylformamide; "NaOEt" is sodium ethoxide; "EtOH" is ethanol; "EtO₂" is diethylether; and "PrOH" is propyl alcohol.

EXAMPLE 1

3-[3-(4-Phenyl-1-Piperidyl)Propyl]-5-Phenyl-5-(2-Pyridyl)Hydantoin.

5-Phenyl-5-(2-pyridyl)hydantoin (6.1 g, 0.024 mol) in 50 ml of DMF was added to a solution of NaOEt (0.048 mol) in 200 ml of absolute EtOH. After addition of 1-(3-chloropropyl)-4-phenyl-piperidine hydrochloride (6.6 g, 0.024 mol), the mixture was heated to reflux with stirring for 18 hours, filtered, and diluted with water. The crystalline solid was collected and recrystallized from aqueous-MeOH-DMF. Yield: 9.3 g (85%); mp 168-9° C.

Analysis — Calculated for $C_{28}H_{30}N_4O_2$: C, 73.98; H, 6.65; N, 12.32. Found: C. 73.48; H, 6.78; N, 12.25.

The free base (5 g, 0.011 mol) was converted to the maleate in MeOH-Et₂O and recrystallized from MeOH-Et₂O. Yield: 5.1 g (81.2%); mp 208° C.

Analysis — Calculated for $C_{32}H_{34}N_4O_6$: C, 67.36; H, 6.00; N, 9.82. Found: C, 67.60; H, 6.16; N, 10.01. Substitution of 1-(2-chloroethyl)-4-phenyl-piperidine or 1-(chloromethyl)-4-phenyl-piperidine for 1-(3-chloropropyl)-4-phenyl-piperidine in the above example respectively yields: 3-[2-(4-phenyl-1-piperidyl)ethyl]-5-phenyl-5-(2-pyridyl)-hydantoin and 3-[(4-phenyl)-1-piperidyl)methyl]-5-phenyl-5-(2-pyridyl)-hydantoin.

EXAMPLE 2

3-[3-(4-Hydroxy-4-Phenyl-1-Piperidyl)Propyl]-5-Phenyl-5-(2-Pyridyl)Hydantoin.

5-Phenyl-5-(2-pyridyl)hydantoin (1.75 g, 0.0069 mol) in 50 ml of DMF was added to a solution of NaOEt (0.0138 mol) in 100 ml of absolute EtOH. After addition of 1-(3-chloropropyl)-4-hydroxy-4-phenylpiperidine hydrochloride (2 g, 0.0069 mol), the mixture was heated to reflux with stirring for 6 hours, filtered, and diluted with water. The free base was twice recrystallized from aqueous-MeOH. Yield: 2.6 g (80.3%) mp 154°–5° C.

Analysis — Calculated for $C_{28}H_{30}N_4O_3$: C, 71.47; H, 6.42; N, 11.91. Found: C, 70.85, H, 6.61; N, 12.02.

The free base (2.4 g, 0.0051 mol) was converted to the maleate in MeOH-Et$_2$O and the salt was recrystallized propyl)-4-phenyl-piperidine hydrochloride (7.6 g, 0.028 mol) the mixture was heated to reflux with stirring for 8 hours, filtered and diluted with water. The solid was triturated in dilute NaOH, collected, and recrystallized from aqueous MeOH. Yield: 9 g (70.7%), mp 150°–152° C.

TABLE C

| 1-(Ω-CHLOROALKYL)-4-SUBSTITUTED-PIPERIDINE | 3-SUBSTITUTED-5-PHENYL-5-(2-PYRIDYL)HYDANTOIN |
| --- | --- |
| 1-(3-chloropropyl)-4-methoxy-4-phenyl-piperidine | 3-[4-methoxy-4-phenyl-1-piperidyl)propyl]-5-phenyl-5-(2-pyridyl)hydantoin |
| 1-(3-chloropropyl)-4-propoxy-4-phenyl-piperidine | 3-[3-(4-propoxy-4-phenyl-1-piperidyl)propyl]-5-phenyl-5-(2-pyridyl)hydantoin |
| 1-(2-chloroethyl)-4-hydroxy-4-phenyl-piperidine | 3-[2-hydroxy-4-phenyl-1-piperidyl)ethyl]-5-phenyl-5-(2-pyridyl)hydantoin |
| 1-(2-chloroethyl)-4-methoxy-4-phenyl-piperidine | 3-([2-(4-methoxy-4-phenyl-1-piperidyl)ethyl]-5-phenyl-5-(2-pyridyl)hydantoin |
| 1-(2-chloroethyl)-4-propoxy-4-phenyl-piperidine | 3-[2-(4-propoxy-4-phenyl-1-piperidyl)ethyl]-5-phenyl-5-(2-pyridyl)hydantoin |
| 1-chloromethyl-4-hydroxy-4-phenyl-piperidine | 3-[(4-hydroxy-4-phenyl-1-piperidyl)ethyl]-5-phenyl-5-(2-pyridyl)hydantoin |
| 1-chloromethyl-4-methoxy-4-phenyl-piperidine | 3-[(4-methoxy-4-phenyl-1-piperidyl)ethyl]-5-phenyl-5-(2-pyridyl)hydantoin |
| 1-chloromethyl-4-propoxy-4-phenyl-piperidine | 3-[4-propoxy-4-phenyl-1-piperidyl)ethyl]-5-phenyl-5-(2-pyridyl)hydantoin | from MeOH—Et$_2$O. Yield: 2.0 g (67%) mp 208°–9° C.

Analysis — Calculated for $C_{32}H_{34}N_4O_7$: C, 65.52; H, 5.82; N, 9.55. Found: C, 65.96; H, 5.85; N, 9.36. Substitution of an appropriate 1-(ω-chloro-alkyl)-4-substituted-piperidine identified in Table C for 1-(3-chloropropyl)-4-hydroxy-4-phenyl-piperidine in the above example yields the corresponding 3-substituted-5-phenyl-5-(2-pyridyl)hydantoin specified in Table C.

EXAMPLE 3

3-[3-(4-Phenyl-1-Piperidyl)Propyl]-5-Phenyl-5-(2-Pyridyl)Hydantoin Methiodide.

3-[3-(4-Phenyl-1-piperidyl)propyl]-5-phenyl-5-(2-pyridyl)hydantoin (2 g, 0.0044 mol) was dissolved in 150 ml of warm absolute EtOH, and methyl iodide (4 ml) was slowly added. The mixture was warmed under gentle reflux for 1 hour and cooled. The salt was collected and recrystallized from MeOH-Et$_2$O. Yield: 1.6 g (611 %); mp 259°–260° C.

Analysis — Calculated for $C_{29}H_{33}IN_4O_2$: C, 58.39; H, 5.57; N, 9.39. Found: C, 58.88; H, 5.77; N, 9.57.

EXAMPLE 4

3-[3-(4-Phenyl-1--Piperidyl)Propyl]-5-Phenyl-5-(3-Pyridyl)-Hydantoin.

5-Phenyl-5-(3-pyridyl)hydantoin (7.1 g, 0.028 mol) in 100 ml of DMF was added to NaOEt (0.056 mol) in 200 ml of absolute EtOH. After the addition of 1-(3-chloro- Analysis — Calculated for $C_{28}H_{30}N_4O_2$: C, 73.98; H, 6.65; N, 12.32. Found: C, 73.44; H, 6.49; N, 12.25.

The free base (4.5 g, 0.01 mol) was converted to the maleate in MeOH-Et$_2$O and was twice recrystallized from MeOHEt$_2$O. Yield: 4.0 g (70.2%), mp 203°–204° C.

Analysis — Calculated for $C_{32}H_{34}N_4O_6$: C, 67.36; H, 6.00; N, 9.82. Found: C, 67.22; H, 6.02; N, 9.76.

Substitution of an appropriate 1-(ω-alkyl)-4-substituted-piperidine identified in Table D for 1-(3-chloropropyl)-phenyl-piperidine in the above procedure yields the corresponding 3-substituted-5-phenyl-5-(3-pyridyl)-hydantoin specified in that table.

Example 5

3-[3-(4-Phenyl-1-Piperidyl)Propyl]-5-Phenyl-5-(4-Pyridyl)Hydantoin.

5-Phenyl-5-(4-pyridyl)hydantoin (7.1 g, 0.028 mol) in 150 ml of DMF was added to NaOEt (0.056 mol) in 200 ml of absolute EtOH, and the resulting mixture was heated to reflux for 30 minutes. After the addition of 1-(3-chloropropyl)-4-phenylpiperidine hydrochloride (7.6 g, 0.028 mol), the mixture was heated to reflux with stirring for 16 hours, filtered, and diluted with water. The free base was collected and recrystallized from aqueous MeOH. Yield: 4.0 g (31.5%), mp 152°–153° C.

TABLE D

| 1-(Ω-CHLOROALKYL)-4-SUBSTITUTED-PIPERIDINE | 3-SUBSTITUTED-5-PHENYL-5-(3-PYRIDYL)HYDANTOIN |
| --- | --- |
| 1-(3-chloropropyl)-4-hydroxy-4-phenyl-piperidine | 3-[3-(4-hydroxy-4-phenyl-1-piperidyl)propyl]-5-phenyl-5-(3-pyridyl)hydantoin |
| 1-(3-chloropropyl)-4-methoxy-4-phenyl-piperidine | 3-[3-(4-methoxy-4-phenyl-1-piperidyl)propyl]-5-phenyl-5-(3-pyridyl)hydantoin |
| 1-(3-chloropropyl)-4-propoxy-4-phenyl-piperidine | 3-[3-(4-propoxy-4-phenyl-1-piperidyl)propyl]-5-phenyl-5-(3-pyridyl)hydantoin |
| 1-(2-chloroethyl)-4-phenyl-piperidine | 3-[2-(4-phenyl-1-piperidyl)ethyl]-5-phenyl-5-(3-pyridyl)hydantoin |
| 1-(2-chloroethyl)-4-hydroxy-4-phenyl-piperidine | 3-[2-(4-hydroxy-4-phenyl-1-piperidyl)ethyl]-5-phenyl-5-(3-pyridyl)hydantoin |
| 1-)2-chloroethyl)-4-methoxy-4-phenyl-piperidine | 3-[2-(4-methoxy-4-phenyl-1-piperidyl)ethyl]-5-phenyl-5-(3-pyridyl)hydantoin |
| 1-(2-chloroethyl)-4-propoxy-4-phenyl-piperidine | 3-[2-(4-propoxy-4-phenyl-1-piperidyl)ethyl]-5-phenyl-5-(3-pyridyl)hydantoin |
| 1-chloromethyl-4-phenyl-piperidine | 3-[(4-phenyl-1-piperidyl)methyl]-5-phenyl-5-(3-pyridyl)hydantoin |
| 1-chloromethyl-4-hydroxy-4-phenyl-piperidine | 3-[(4-hydroxy-4-phenyl-1-piperidyl)ethyl]-5-phenyl-5-(3-pyridyl)hydantoin |
| 1-chloromethyl-4-methoxy-4-phenyl-piperidine | 3-[(4-methoxy-4-phenyl-1-piperidyl)ethyl]-5-phenyl-5-(3-pyridyl)hydantoin |
| 1-chloromethyl-4-propoxy-4-phenol-piperidine | 3-[(4-propoxy-4-phenyl-1-piperidyl)ethyl]-5- |

TABLE D-continued

| 1-(Ω-CHLOROALKYL)-4-SUBSTITUTED-PIPERIDINE | 3-SUBSTITUTED-5-PHENYL-5-(3-PYRIDYL)HYDANTOIN |
|---|---|
| | phenyl-5-(3-pyridyl)hydantoin |

Analysis — Calculated for $C_{28}H_{30}N_4O_2$: C, 73.98; H, 6.65; N, 12.32. Found: C, 73.82; H, 6.45; N, 12.24.

The free base (4 g, 0.0088 mol) was converted to the maleate in MeOH-Et$_2$O and recrystallized from 2-PrOH-MeOHEt$_2$O. Yield: 4.2 g (83.8%), mp 206° C.

Analysis — Calculated for $C_{32}H_{34}N_4O_6$: C, 67.36; H, 6.00; N, 9.82. Found: C, 67.09; H, 6.00; N, 10.09.

Substitution of an appropriate 1-(ω-alkyl)-4-substituted-piperidine identified in Table E for 1-(3-chloropropyl)-4-phenyl-piperidine in the preceding example yields the corresponding 3-substituted-5-phenyl-5-(4-pyridyl)hydantoin presented in that table.

EXAMPLE 6

Antiarrhythmic Activity

The antiarrhythmic activity 3-[3-(4-phenyl-1-piperidyl)propyl]-5-phenyl-5-(2-pyridyl)hydantoin (Example 1), 3-[3-(4-hydroxy-4-phenyl-1-piperidyl)propyl]-5-phenyl-5-(2-pyridyl)hydantoin (Example 2), 3-[3-(4-phenyl-1-piperidyl)propyl]-5-phenyl-5-(2-pyridyl)-hydantoin methiodide (Example 3), 3-[3-(4-phenyl-1-piperidyl)propyl]-5-phenyl-5-(3-pyridyl)-hydantoin (Example 4), and 3-[3-(4-phenyl-1-piperidyl)propyl]-5-phenyl-5-(4-pyridyl)hydantoin (Example 5) was compared to that of 5-phenyl-5-(2-pyridyl)hydantoin (V), 5-phenyl-5-(3-pyridyl)hydantoin (VI), 5-phenyl-5-(4-pyridyl)hydantoin (VII), and quinidine (I). Compounds I, V, VI, and VII are the prior art compounds discussed in the preceding section, "Prior Art".

The antiarrhythmic activity of the compounds listed above were tested in the experimental model reported by J. W. Lawson (J. Pharmacol. Exp. Therap., 160: 22-31 [1968]).

The test compounds were administered in varying intraperitoneal doses to groups consisting of 5 mice. Ten minutes after administration of a given dose of a compound, a mouse was transferred to a covered 300 ml glass beaker that contained a wad of cotton saturated with about 20 ml of chloroform. The animal was observed closely and removed from the beaker immediately after respiratory arrest. The heart was quickly exposed by making an incision through the abdomen, diaphragm, thorax and pericardium for visual inspection of ventricular rate and rhythm. Ventricular contractions were counted for 30 seconds. According to the procedure reported by Lawson, animals with ventricular rate not exceeding 100 contractions during the 30 second observation period were considered protected. Results obtained with each dose were used to calculate the mean effective doses ($ED_{50}$) and 95% confidence limits (95% CL) after the method of Litchfield and Wilcoxon (J. Pharmacol. Exp. Therap., 96: 99-113 [1949]).

$LD_{50}$ data were obtained by standard procedures known to the art.

In Table F, the compounds of this invention are listed by the arabic number corresponding to the example number and the prior art compounds by their assigned Roman numeral. Table F demonstrates that the claimed compounds are more effective than the prior art compounds and have therapeutic indices that are superior to those of the prior art compounds.

TABLE F

Antiarrhythmic Activity of Claimed Compounds and of the Prior Art

| COMPOUND | $ED_{50}$ (95% CL) mg/kg, i.p. | $LD_{50}$ (95% CL) mg/kg, i.p. | THERAPEUTIC INDEX |
|---|---|---|---|
| 1 | 15.3 (8-29) | 136 ( — ) | 9.0 |
| 2 | 19.2 (12-31) | 65 (41-103) | 3.4 |
| 4 | 31.0 (19-51) | 156 ( — ) | 5.0 |
| 5 | 28.0 (18-44) | 61 ( — ) | 2.1 |
| I | 91 (35-237) | 178 (146-216) | 2.0 |
| V | 160 (92-282) | 186 ( — ) | 1.16 |
| VI | >310* | — | — |
| VII | 205 (132-318) | 240 (142-403) | 1.17 |

TABLE E

| 1-(Ω-CHLOROALKYL)-4-SUBSTITUTED-PIPERIDINE | 3-SUBSTITUTED-5-PHENYL-5-(4-PYRIDYL)HYDANTOIN |
|---|---|
| 1-(3-chloropropyl)-4-hydroxy-4-phenyl-piperidin | 3-[3-(4-hydroxy-4-phenyl-1-piperidyl)propyl]-5-phenyl-5-(4-pyridyl)hydantoin |
| 1-(3-chloropropyl)-4-methoxy-4-phenyl-piperidine | 3-[3-(4-methoxy-4-phenyl-1-piperidyl)propyl]-5-phenyl-5-(4-pyridyl)hydantoin |
| 1-(3-chloropropyl)-4-propoxy-4-phenyl-piperidine | 3-[3-(4-propoxy-4-phenyl-1-piperidyl)propyl]-5-phenyl-5-(4-pyridyl)hydantoin |
| 1-(2-chloroethyl)-4-phenyl-piperidine | 3-[2-(4-phenyl-1-piperidyl)ethyl]-5-phenyl-5-(4-pyridyl)hydantoin |
| 1-(2-chloroethyl)-4-hydroxy-4-phenyl-piperidine | 3-[2-(4-hydroxy-4-phenyl-1-piperidyl)ethyl]-5-phenyl-5-(4-pyridyl)hydantoin |
| 1-(2-chloroethyl)-4-methoxy-4-phenyl-piperidine | 3-[2-(4-methoxy-4-phenyl-1-piperidyl)ethyl]-5-phenyl-5-(4-pyridyl)hydantoin |
| 1-(2-chloroethyl)-4-propoxy-4-phenyl-piperidine | 3-[2-(4-propoxy-4-phenyl-1-piperidyl)ethyl]-5-phenyl-5-(4-pyridyl)hydantoin |
| 1-chloromethyl-4-phenyl-piperidine | 3-[(4-phenyl-1-piperidyl)methyl]-5-phenyl-5-(4-pyridyl)hydantoin |
| 1-chloromethyl-4-hydroxy-4-phenyl-piperidine | 3-[(4-hydroxy-4-phenyl-1-piperidyl)ethyl]-5-phenyl-5-(4-pyridyl)hydantoin |
| 1-chloromethyl-4-methoxy-4-phenyl-piperidine | 3-[(4-methoxy-4-phenyl-1-piperidyl)ethyl]-5-phenyl-5-(4-pyridyl)hydantoin |
| 1-chloromethyl-4-propoxy-4-phenyl-piperidine | 3-[(4-propoxy-4-phenyl-1-piperidyl)ethyl]-5-phenyl-5-(4-pyridyl)hydantoin |

*2 of 5 mice were protected at this dose.

What is claimed is:

1. In a therapeutic method of treating a cardiac arrhythmia in an individual in whom such therapy is indicated by administration of an antiarrhytmic agent, the improvement comprising:
   administering to the individual an effective antiarrhythmic amount of a compound having the formula,

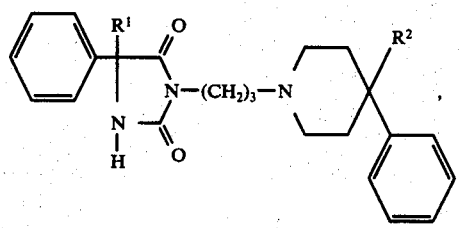

or a pharmacologically acceptable, non-toxic salt thereof, in which:

R¹ is selected from the group consisting of 2-pyridyl, 3-pyridyl, or 4-pyridyl radicals; and R² is selected from the group consisting of a hydrogen atom or a hydroxyl group.

2. The method as in claim 1, wherein the compound is 3-[3-(4-phenyl-1-piperidyl)propyl]-5-phenyl-5-(2-pyridyl)-hydantoin.

3. The method as in claim 1, wherein the compound is 3-[3-(4-phenyl-1-piperidyl)propyl]-5-phenyl-5-(2-pyridyl)-hydantoin maleate.

4. The method as in claim 1, wherein the compound is 3-[3-(4-hydroxy-4-phenyl-1-piperidyl)propyl]-5-phenyl-5-(2-pyridyl)hydantoin.

5. The method as in claim 1, wherein the compound is 3-[3-(4-hydroxy-4-phenyl-1-piperidyl)propyl]-5-phenyl-5-(2-pyridyl)hydantoin maleate.

6. The method as in claim 1, wherein the compound is 3-[3-(4-phenyl-1-piperidyl)propyl]-5-phenyl-5-(2-pyridyl)-hydantoin methiodide.

7. The method as in claim 1, wherein the compound is 3-[3-(4-phenyl-1-piperidyl)propyl]-5-phenyl-5-(3-pyridyl)-hydantoin.

8. The method as in claim 1, wherein the compound is 3-[3-(4-phenyl-1-piperidyl)propyl]-5-phenyl-5-(3-pyridyl)-hydantoin maleate.

9. The method as in claim 1, wherein the compound is 3-[3-(4-phenyl-1-piperidyl)propyl]-5-phenyl-5-(4-pyridyl)-hydantoin.

10. The method as in claim 1, wherein the compound is 3-[3-(4-phenyl-1-piperidyl)propyl]-5-phenyl5-(4-pyridyl)-hydantoin maleate.

* * * * *